United States Patent [19]

Nishimura

[11] Patent Number: 5,543,062

[45] Date of Patent: Aug. 6, 1996

[54] LEUKOCYTE-REMOVING FILTER DEVICE AND SYSTEM AND METHOD OF USING THEREOF

[75] Inventor: Takao Nishimura, Oita, Japan

[73] Assignee: Asahi Medical Co., Ltd., Tokyo, Japan

[21] Appl. No.: 559,726

[22] Filed: Nov. 15, 1995

Related U.S. Application Data

[63] Continuation of Ser. No. 132,894, Oct. 7, 1993, abandoned.

[30] Foreign Application Priority Data

Oct. 7, 1992 [JP] Japan ................................. 4-291950

[51] Int. Cl.$^6$ ........................... B01D 21/26; B01D 36/00; B01D 37/00

[52] U.S. Cl. ................ 210/782; 210/257.1; 210/321.75; 210/321.84; 210/435; 210/443; 210/453; 210/767; 210/806; 494/36; 494/37; 604/406; 604/408; 604/410

[58] Field of Search ............................... 210/252, 257.1, 210/321.75, 321.84, 433.1, 435, 443, 453, 488, 496, 497.01, 767, 782, 787, 789, 800, 806; 422/101; 494/16, 20, 21, 37, 36; 604/4, 5, 406, 408, 410

[56] References Cited

U.S. PATENT DOCUMENTS

| | | | |
|---|---|---|---|
| 1,608,966 | 11/1926 | Tanaka | 210/443 |
| 4,228,011 | 10/1980 | Cote, Jr. | 210/443 |
| 4,596,657 | 6/1986 | Wisdom | 210/206 |
| 4,701,267 | 10/1987 | Watanabe et al. | 210/806 |
| 4,767,541 | 8/1988 | Wisdom | 210/749 |

(List continued on next page.)

FOREIGN PATENT DOCUMENTS

| | | |
|---|---|---|
| 4022700 | 1/1992 | Germany. |
| 9104088 | 4/1991 | WIPO. |
| 9220427 | 11/1992 | WIPO. |
| 9220428 | 11/1992 | WIPO. |

OTHER PUBLICATIONS

"Biomedical Applications of Polymeric . . . ," edited by T. Tsuruta et al. CRC Press, 1993, pp. 191–218.

"Plasma Exchange Therapy – Plasmapheresis '88," edited by S. Koshikawa, with English translation thereof, pp. 114–115.

"The Role of Leucocyte Depletion . . . ," edited by B. Brozović, Blackwell Scientific Publ., 9 Jul. 1988, pp. 1–3, 23–45, 48–50, 66–73, 80, 89.

"Controversies of Leukocyte–Poor . . . ," edited by L. J. McCarthy et al., American Assoc. of Blood Banks, 1989, pp. 12–15, 35–41, 56–65.

"Clinical Application of Leukocyte Depletion," edited by S. Sekiguchi, Blackwell Scientific Publ., 1993, pp. 47–62, 138–148, 193–201.

*Primary Examiner*—John Kim
*Attorney, Agent, or Firm*—Birch, Stewart, Kolasch & Birch, LLP

[57] ABSTRACT

Disclosed is a leukocyte-removing filter device comprising (a) a casing having an inlet for blood and an outlet for leukocyte-removed blood, which are both located in a top portion of the casing, and (b) a filter medium disposed in the casing so as to divide the internal space of the casing into an inlet-side chamber communicated with the inlet and an outlet-side chamber communicated the outlet. By virtue of the locations of the inlet and outlet on the top portion of the filter device, the leukocyte-removing filter device of the present invention is advantageous not only in that the filter device can be fittedly and stably accommodated into a centrifuge cup together with a plurality of blood bags and circuit tubes connecting the filter device and blood bags, so that a centrifugation can be efficiently conducted without the danger of damaging the filter device and the blood bags, but also in that the operation of expelling the air from the filter by filling the filter with blood can be very readily conducted simply by allowing blood to flow into the filter without any additional burdensome operations. The leukocyte-removing system comprising the above-mentioned leukocyte-removing filter device is also disclosed.

16 Claims, 7 Drawing Sheets

U.S. PATENT DOCUMENTS

| | | | |
|---|---|---|---|
| 4,810,378 | 3/1989 | Carmen et al. | 210/206 |
| 4,880,548 | 11/1989 | Pall et al. | 210/767 |
| 4,915,848 | 4/1990 | Carmen et al. | 210/749 |
| 4,919,823 | 4/1990 | Wisdom | 210/749 |
| 4,923,620 | 5/1990 | Pall | 210/767 |
| 4,925,572 | 5/1990 | Pall | 210/767 |
| 4,936,998 | 6/1990 | Nishimura et al. | 210/638 |
| 4,985,153 | 1/1991 | Kuroda et al. | 210/782 |
| 4,997,577 | 3/1991 | Stewart | 210/767 |
| 5,089,146 | 2/1992 | Carmen et al. | 210/782 |
| 5,092,996 | 3/1992 | Spielberg | 210/232 |
| 5,100,564 | 3/1992 | Pall et al. | 210/782 |

LEUKOCYTE-REMOVING FILTER DEVICE AND SYSTEM AND METHOD OF USING THEREOF

This application is a continuation of application Ser. No. 08/132,894 filed on Oct. 7, 1993, now abandoned.

BACKGROUND OF THE INVENTION

Field of The Invention

The present invention relates to a filter device for removing leukocytes. More particularly, the present invention is concerned with a leukocyte-removing filter device comprising (a) a casing having an inlet for blood and an outlet for leukocyte-removed blood, which are both located in a top portion of the casing, and (b) a filter medium disposed in the casing so as to divide the internal space of the casing into an inlet-side chamber communicated with the inlet and an outlet-side chamber communicated with the outlet. By virtue of the specific locations of the inlet and outlet of the filter device, the leukocyte-removing filter device of the present invention is advantageous not only in that the filter device can be fittedly and stably accommodated in a centrifuge cup together with a plurality of blood bags and circuit tubes connecting the filter device and blood bags, so that a centrifugation can be efficiently conducted without the danger of damaging the filter device and the blood bags, but also in that the operation of expelling the air from the filter by filling the filter with blood can be very readily performed simply by allowing blood to flow into the filter without any additional burdensome operations. In addition, this filter is simple in structure and, therefore, is easy to produce. The present invention is also concerned with a leukocyte-removing system comprising this novel leukocyte-removing filter device, inlet connecting means fluid-tightly connected to the inlet of the filter device for aseptically connecting a part preceding the filter device to the inlet of the filter device, and outlet connecting means for connecting the outlet of the filter device to at least one blood bag.

Discussion of Related Art

In recent years, in the field of blood transfusion, a leukocyte-free blood transfusion, in which a blood material, from which leukocytes have been removed by means of a leukocyte-removing filter, is employed for transfusion, is increasingly carried out. This is because it has been elucidated that side effects of transfusion, such as non-hemolytic feverish reactions (headache, nausea, and chills), and side effects more serious to a recipient, such as allosensitization, post-transfusion GVHD (graft versus host disease) and viral infection, are mainly caused by leukocytes contained in a blood material employed for transfusion (see, for example, Brozovic, B., The Role of Leucocyte Depletion in Blood Transfusion, Blackwell Scientific Publications, Oxford, 1989.; McCarthy, L. J. and Baldwin, M. L., Controversies of Leukocyte-Poor Blood and Components, American Association of Blood Banks, Virginia, 1989.; and Sekiguchi, S., Clinical Application of Leukocyte Depletion, Blackwell Scientific Publications, Cambridge, 1993).

As a means for removing leukocytes from blood materials (such as whole blood, red cell concentrate, and platelet concentrate), various filters comprising a casing having an inlet for blood and an outlet for leukocyte-removed blood and, packed in the casing, a filter medium for removing leukocytes, have been put to practical use (see, for example, U.S. Pat. Nos. 4,701,267, 4,936,998, 4,880,548, 4,923,620, and 4,925,572).

A blood transfusion can be conducted by, for example, a method in which whole blood is taken from a healthy person; the whole blood is subjected to appropriate treatment, such as centrifugation, thereby obtaining a blood product for transfusion; the blood product is stored until the time of use; and the blood product is subjected to leukocyte removal treatment just before use; and the leukocyte-removed blood product is transfused into a patient. However, it is known that from the viewpoint of obtaining a blood product of high quality, it is desired that leukocyte removal be conducted before the storing of the blood, but not after the storing thereof. Accordingly, various systems containing a leukocyte-removing filter have been proposed for removing leukocytes from blood before the storing of the blood (see, for example, U.S. Pat. Nos. 4,596,657, 4,767,541, 4,919,823, 4,810,378, 4,915,848, 5,092,996, 5,100,564, 5,089,146, 4,985,153, and 4,997,577, WO 92/20427, WO 92/20428, WO 91/04088, and German Patent Application 4022700 A1). The conventional leukocyte-removing filters used in these known systems have an inlet and an outlet which are, respectively, located at opposite ends (upper and lower ends) of the filter.

In general, a leukocyte-removing system containing a leukocyte-removing filter, which can be used for removing leukocytes from blood before the storing of the blood, is a multiple blood bag system comprising a primary bag (as a blood collection bag), and a plurality of satellite bags, one of which is connected to the primary bag (blood collection bag) through a leukocyte-removing filter means (see, for example, U.S. Pat. No. 4,596,657, U.S. Pat. No. 5,089,146, WO 91/04088, and German Patent Application 4022700A1). The use of such leukocyte-removing systems involves an operation in which blood is collected in the primary bag and the primary bag containing the blood is placed in a centrifuge together with the filter means and the satellite bags, and the blood is subjected to centrifugation so as to be separated into a plasma layer and an erythrocyte concentrate layer.

However, actual experiments conducted using the conventional leukocyte-removing systems, have revealed that due to the structure of the filter in which the inlet and the outlet (connected respectively to the primary bag and one of the satellite bags through conduit means) are located at opposite ends (upper and lower ends) of the filter, not only is the handling of the filter cumbersome, but also it is very difficult to fittedly and stably accommodate the filter in a centrifuge cup together with the primary bag and the satellite bags. For example, when the filter is placed above the blood bags in the centrifuge cup, the filter is unstable in the centrifuge cup, so that there is a danger that the filter is likely to be out of the centrifuge cup. For preventing the filter from being out of the centrifuge cup, it is necessary to fix the filter to the centrifuge cup together with the blood bags by means of an adhesive tape after the filter has been placed above the blood bags, thereby securing the entire system to the centrifuge cup. This operation is extremely cumbersome. On the other hand, when the filter is placed directly on the bottom of the centrifuge and under the blood bags, or the filter is placed between blood bags arranged one upon another, or the filter is placed between blood bags arranged side by side, it is difficult to compactly, fittedly and stably accommodate the entire filter system in the centrifuge, leading to a danger that the filter and the bags are likely to be destroyed due to the centrifugal force and the friction between the bags and the filter during centrifugation.

In order to solve the above problems, U.S. Pat. No. 5,100,564 discloses the use of a support means provided around the upper circumference of the centrifuge cup, which supports the filter under the centrifugal force. However, the use of such a support means is cumbersome, so that this technique has not been widely used.

U.S. Pat. No. 5,092,996 also discloses the use of a support means which has the same function as that disclosed in the above-mentioned U.S. Pat. No. 5,100,564. In U.S. Pat. No. 5,092,996, a flange (support means) is formed around the periphery of the filter in unified fashion so that the flange of the filter engages the upper circumference of the centrifuge cup when the filter is inserted in the centrifuge cup. However, the configuration of the filter becomes complicated due to the provision of the flange, so that difficulties occur in handling the filter. Further, even in the case of this technique, the danger that the filter is likely to be out cannot be completely removed without the use of a fixing means, such as an adhesive tape, for fixing the filter to the centrifuge cup.

Meanwhile, irrespective of whether it is before or after the storing of blood, when a leukocyte-removing filter is actually used for filtering the blood, it is necessary to expel the air from the filter by filling the filter with the blood at the time of start of the filtering operation. The purpose of the air-expelling operation is to allow the blood to flow uniformly and smoothly through the entire filler material in the filter, thereby preventing a decrease in the effective filtering area, so that not only can the leukocyte removing capability be fully exerted, but also a desired flow rate of blood can be maintained.

As mentioned above, in conventional leukocyte-removing filters, the inlet and the outlet are, respectively, located at opposite ends (upper and lower ends) of the filter (see, for example, U.S. Pat. Nos. 4,701,267 and 4,936,998). In the case of the leukocyte-removing filters in which the inlet and the outlet are, respectively, located at the upper and lower ends, the above-mentioned air-expelling operation is generally conducted by either a method in which before blood is flowed, the filter is held upside down so that the locations of the inlet and the outlet are reversed and the filter is filled with blood by flowing blood from the bottom up to the top of the filter, or a method in which blood is forcibly introduced into the filter (held in normal position) by strongly squeezing the (blood-containing) blood collection bag connected to the inlet of the filter, thereby forcibly increasing the flow rate of blood in the filter. However, the former is cumbersome and, therefore, this method is not desired by medical workers, who are usually very busy. Further, the latter poses a danger that hemolysis of the blood material and a lowering of the leukocyte-removing capability of the filter are likely to occur.

U.S. Pat. No. 4,923,620 discloses a filter for removing leukocytes, wherein the inlet and the outlet are, respectively, located at lower and upper ends of the filter. This filter is advantageous in that cumbersome air-expelling operations, such as holding the filter upside down, are not required. However, this filter has an extremely complicated structure, so that the filter cannot be easily produced and the inlet and outlet of this filter are likely to be destroyed during operation. Further, this filter is disadvantageous in that when a blood collection bag containing whole blood is placed in a centrifuge cup together with the filter and at least one satellite bag for collecting treated blood and then, the blood is subjected to centrifugation, the filter and the bags are likely to be damaged due to the centrifugal force and the friction between the bags and the filter during the centrifugation.

Summary of the Invention

The present inventor has made extensive and intensive studies with a view toward developing a novel leukocyte-removing filter device, and a system containing the same, which are free from the above-mentioned drawbacks inevitably accompanying the conventional leukocyte-removing filters and systems. As a result, it has unexpectedly been found that when in a leukocyte-removing system is incorporated a filter device having an inlet for blood and an outlet for leukocyte-removed blood which are both located in a top portion of the casing, damages of the blood bags can be effectively avoided during centrifugation. It has also been found that by virtue of the above-mentioned specific locations of the inlet and the outlet of the filter device, the air in the filter device can be effectively expelled without any additional burdensome operations, such as holding a filter upside down or squeezing a blood collection bag preceding to the filter device. Based on these novel findings, the present invention has been completed.

Accordingly, it is an object of the present invention to provide a leukocyte-removing filter device which is not only unlikely to be damaged during centrifugation, but is also easy to expel the air therefrom, while having excellent capability to remove leukocytes from blood to thereby obtain high quality leukocyte-removed blood product or products.

It is another object of the present invention to provide a leukocyte-removing system which can be advantageously used for efficiently and effectively removing leukocytes from blood to thereby obtain high quality leukocyte-removed blood product or products.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only and, thus, are not limitative of the present invention, and wherein.

DETAILED DESCRIPTION OF THE INVENTION

According to the present invention, there is provided a leukocyte-removing filter device comprising:

(a) a flat casing comprising opposite flat main walls fluid-tightly connected by a side wall structure to define an internal space of the casing, the casing having a top and a bottom portion which are spaced apart vertically of the casing, the top portion having an inlet for blood and an outlet for leukocyte-removed blood, and (b) a filter medium comprising at least one filter material sheet extending in the internal space of the casing along the flat main walls to partition the internal space into an inlet-side chamber communicated with the inlet and an outlet-side chamber communicated with the outlet.

In the present invention, the term "blood" used herein includes not only whole blood but also leukocyte-containing suspensions, such as a leukocyte-containing red cell product and a leukocyte-containing platelet product.

Figure 1:
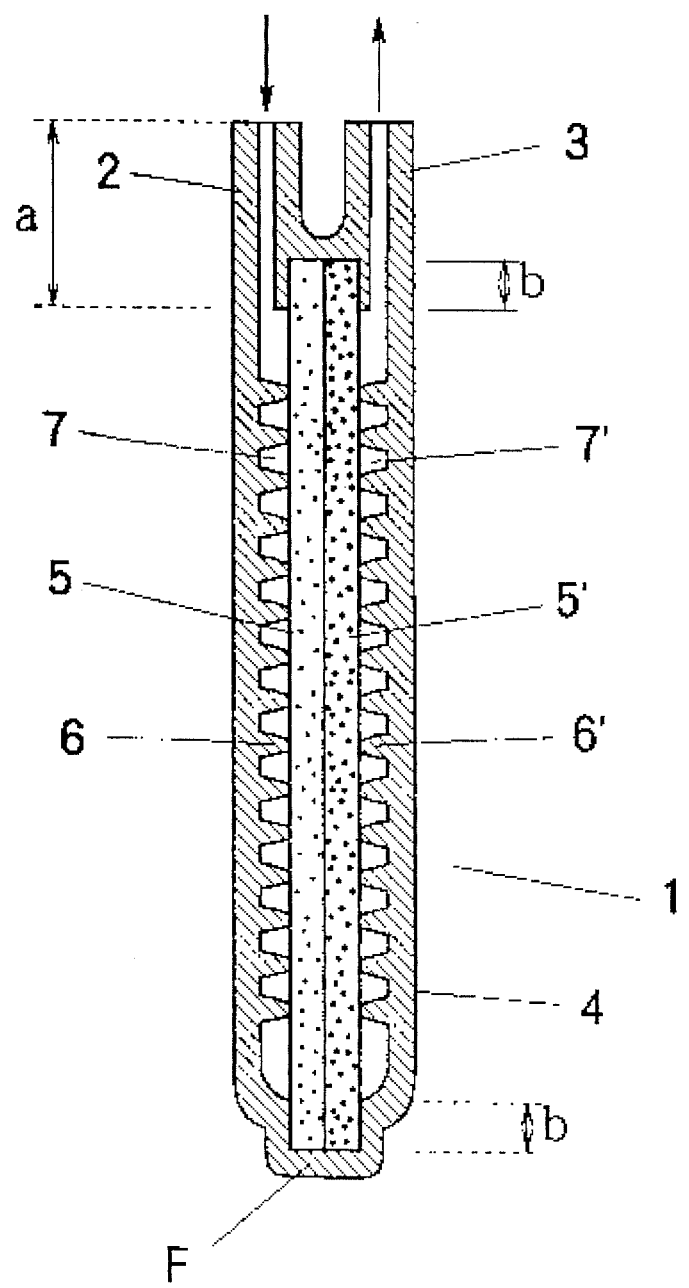
FIG. 1 is an enlarged, cross-sectional view of the filter device shown in FIG. 2(a), taken along line I—I of FIG. 2(a)
Figure 2A:
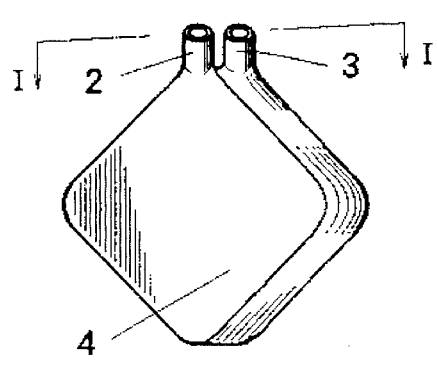
FIGS. 2(a) to 2(f) are diagrammatic perspective views of various forms of the filter device of the present invention.
Figure 2B:
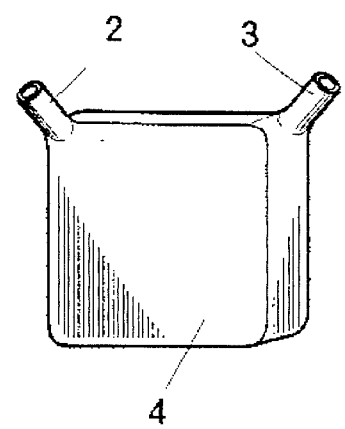

Referring now to FIG. 1 showing an enlarged, cross-sectional view of the filter device shown in FIG. 2(a), taken along line I—I of FIG. 2(a), filter device 1 comprises flat casing 4 and a filter medium. Flat casing 4 comprises opposite flat main walls fluid-tightly connected by flange-shaped side wall structure F to define the internal spacing of casing 4. Flat casing 4 has a top portion and a bottom portion which are spaced apart vertically of the casing. The top portion of casing 4 has nozzle-shaped inlet 2 for blood and nozzle-shaped outlet 3 for leukocyte-removed blood. Over the entire length of the inner side of flange-shaped side wall structure F is formed a groove having a depth of b. The filter medium comprises a double layer of filter material sheets 5,5'. The entire peripheral edge of the filter medium is inserted in the above-mentioned groove, so that the filter medium extends in the internal space of casing 4 along the flat main walls to partition the internal space into inlet-side chamber 7 communicated with inlet 2 and outlet-side chamber 7' communicated with outlet 3.

Each of the inlet-side chamber 7 and the outlet-side chamber 7' may have therein pressing means for pressing the filter medium in a direction opposite to an inner wall surface of the respective flat main wall of casing 4 to thereby securely support the filter medium in the inner space of casing 4. In the embodiment shown in FIG. 1, the pressing means comprises a plurality of projections 6, 6' formed in spaced relationships on the inner wall surface of the respective flat main wall of casing 4, wherein the projections 6, 6' extend in a direction toward the filter medium. The configuration of the pressing means is not limited to that shown in FIG. 1, and any alternative structures can be used. For example, the pressing means may comprise a loose mesh-like structure resiliently disposed between the filter medium and the inner wall surface of the respective flat main wall of casing 4. In the filter device of the present invention, when pressing means is employed for supporting the filter medium as shown in FIG. 1, it is preferred that the volume of the pressing means be not more than 5%, based on the volume of each of the inlet-side chamber and the outlet-side chamber of the filter device.

In the filter device of the present invention, it is essential that both of the inlet for blood and the outlet for leukocyte-removed blood be located in the top portion of the casing of the filter device. The term "top portion" used herein means a portion of the casing which corresponds to one-third or less (preferably one-fifth or less, more preferably one-tenth or less) the vertical length of the casing as measured from the top end of the casing. It is most preferred that the top portion be a portion as close to the top end of the casing as possible. When the inlet and outlet have a configuration having a portion protruding out of a contour of the main body of the casing (e.g., when the inlet and outlet are nozzle-shaped ones provided at the top of the casing), the protruded portions are excluded in defining the locations of the inlet and outlet.

The term "flat casing" means a casing having flat main walls fluid-tightly connected by a side wall structure, in which the width or height of the main walls, whichever is shorter, is preferably at least two times the width of the side wall structure (i.e., thickness of the flat casing), more preferably at least four times the width of the side wall structure.

Figure 2C:
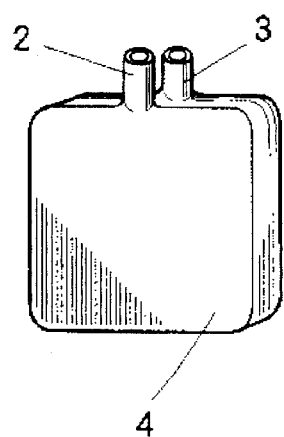

The flat casing of the present invention may have a plurality of sides, in which the inlet and outlet are located at corners formed between sides of the casing at a same upper corner or at different upper corners as shown in FIGS. 2(a), 2(b), 2(d) and 2(f), or located on the upper side of the casing as shown in FIG. 2(c). Alternatively, the casing may have a drum-shaped structure comprised of substantially circular flat main walls connected by an annular side wall structure, in which the inlet and outlet are located on the annular wall structure as shown in FIG. 2(e). In each of FIGS. 2(a) to 2(f), the side wall structure is shown not in a flange-shaped configuration indicated by character F in FIG. 1 but only in a flat configuration for the sake of simplicity. In this connection, however, it is to be noted that the side wall structure can have a flat configuration as shown in FIGS. 2(a) to 2(f).

The contour of the flat casing of the filter device of the present invention generally corresponds to the configuration of the blood-flowing interior of the casing, which includes an inlet-side and an outlet-side chamber and the filter medium disposed therebetween, and the size of the flat casing is a little larger than that of the blood-flowing interior of the casing.

In the filter device of the present invention, the inlet opens in a direction along a first line and the outlet opens in a direction along a second line, wherein the first and second lines each forms an angle with a central axis vertically extending from the top portion to the bottom portion.

In the filter of the present invention, as mentioned above, the top portion has both an inlet for blood and an outlet for leukocyte-removed blood. Therefore, the filter device of the present invention can be easily and stably accommodated in a centrifuge cup together with a plurality of bags including a blood collection bag, as compared to the conventional leukocyte-removing filter in which an inlet for blood and an outlet for a leukocyte-removed blood are located at opposite sides of the casing, respectively.

Figure 4:
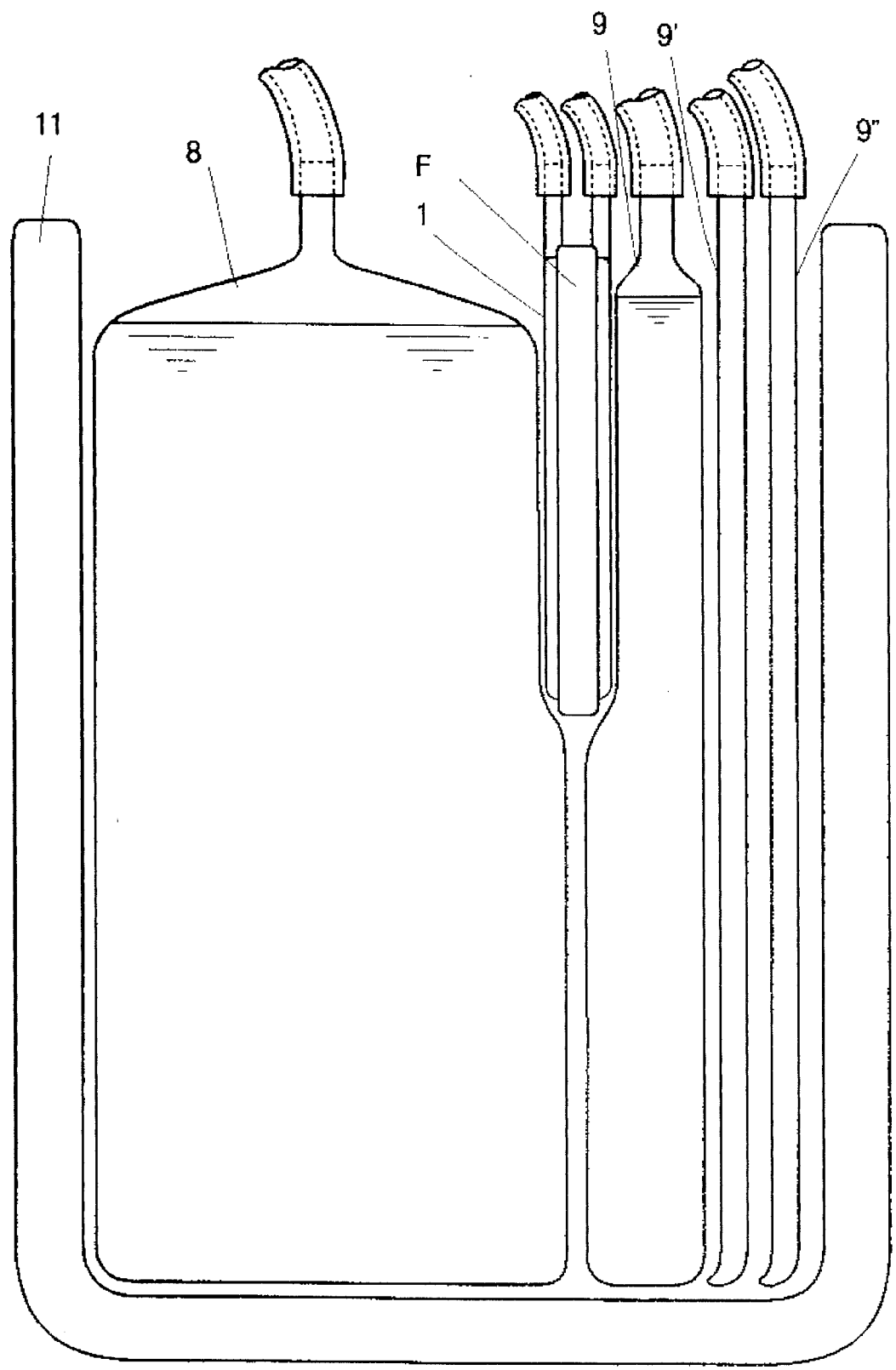
FIG. 4 is a diagrammatic view showing a manner in which the leukocyte-removing system containing the leukocyte-removing filter device shown in FIG. 2(a) of the present invention, is stably accommodated in a centrifuge cup, with a front side of the centrifuge cup taken away to show the interior of the centrifuge cup.

For example, as shown in FIG. 4, filter device 1 can be easily and stably placed between blood collection bag 8 and a set of satellite bags 9, 9' and 9" in centrifuge cup 11 (wherein blood collection bag 8 contains whole blood, satellite bag 9 contains a preservative liquid for red cell concentrate, satellite bags 9', 9" are empty) by virtue of the location of the inlet and outlet of the filter device in the top portion of the casing Of the filter device.

FIG. 4 is a diagrammatic view showing a manner in which the leukocyte-removing system as shown in FIG. 5(*b*), is stably accommodated in centrifuge cup 11, with a front side of the centrifuge cup taken away to show the interior of the centrifuge cup. In FIG. 4, filter device 1 of FIG. 2(*a*) is positioned so that a side of the casing as viewed in a direction indicated by a broken arrow in FIG. 2(*a*) can be seen as the flange-shaped side wall structure (F) in FIG. 4. As shown in FIG. 5(*b*), blood collection bag 8 has a couple of outlets, one of which is connected to satellite bags 9', 9" and the other of which is connected to satellite bag 9 through filter device 1. In FIG. 4, only the former is indicated and the latter is omitted.

In FIG. 4, filter device 1 is placed in a vertically directed configuration between blood collection bag 8 and satellite bag 9. Alternatively, filter device 1 may be placed in a horizontally directed configuration on blood collection bag 8. In this case too, the system including the filter device and various blood bags can be easily accommodated in a centrifuge cup, since the inlet and outlet of the filter device are positioned on and directed toward the same side. In FIG. 4, satellite bag 9 containing a preservative liquid is illustrated in a slim form, in which the preservative liquid is filled up to a high level. However, satellite bag 9 can be expanded to substantially the same size as that of blood collection bag 8. Therefore, satellite bag 9 can receive therein leukocyte-removed blood from filter device 1.

As mentioned above, in the case of the conventional leukocyte-removing filters wherein the inlet for blood and the outlet for leukocyte-removed blood are positioned on opposite sides, when a filter is packed in a centrifuge cup together with a plurality of bags in a manner shown in FIG. 4 except that one of the inlet and outlet of the filter is located at a top portion of the casing and the other is located at a bottom portion of the casing, and the resultant system is then subjected to centrifugation, the filter is sometimes moved downward due to the action of the centrifugal force or the like and the inlet or the outlet disposed at the bottom of the casing of the filter is likely to be heavily pressed to the bottom wall of the centrifuge cup, so that the inlet or the outlet positioned at the bottom portion of the filter is likely to be destroyed. Even when the downward movement of the filter is not so large and therefore the filter is not pressed directly to the bottom wall of the centrifuge cup, the filter is caused to thrust the blood collection bag downward due to centrifugal force, so that the blood collection bag is likely to become damaged.

By contrast, by virtue of the characteristic feature of the filter device of the present invention wherein both the inlet for blood and the outlet for a leukocyte-removed blood are located in the top portion of the casing, the filter device of the present invention can be easily and stably packed in a centrifuge cup together with a plurality of blood bags including circuit tubes connecting them, without the danger of suffering damage during the centrifuge operation. This advantage is enhanced by another feature in that the inlet and the outlet each form an angle with the central axis of the casing, wherein each angle is independently not more than 90° inclusive of 0° relative to the central axis.

Further, the filter device of the present invention is advantageous in that the air in the filter device can be readily expelled simply by allowing blood to flow into the filter device without any additional burdensome operations.

In the case of the conventional leukocyte-removing filters in which the inlet and the outlet are, respectively, located on opposite sides (upper and lower sides) of the filter, the air-expelling operation is conducted by either a method before blood is allowed to flow, in which the filter is held upside down so that the locations of the inlet and the outlet are reversed and the filter is filled with blood by flowing from the bottom up to the top of the filter; or a method in which blood is forcibly introduced into the filter (held in normal position) by strongly squeezing the blood bag containing the blood connected to the inlet of the filter, thereby forcibly increasing the flow rate of blood in the filter. The former is cumbersome and, therefore, this method is not desired by medical workers, who are usually very busy. The latter poses the danger that hemolysis of the treated blood material and a lowering of leukocyte-removing capability are likely to occur.

Furthermore, in the case of the conventional filters, if the air-expelling operation by using either of the above-mentioned two burdensome methods is not conducted, the air present in the upper portion of the filter medium and in the upper portion of the outlet-side chamber cannot be readily expelled simply by allowing blood to flow into the filter from the inlet provided in the upper end of the casing through the outlet provided in the lower end of the casing.

By contrast, in the filter device of the present invention, when blood is allowed to flow into the filter device through inlet 2 shown in FIG. 1, the blood readily fills the entire internal space of the filter device and flows out of the filter device through outlet 3 while expelling all of the air through outlet 3. Therefore, in the present invention, there is no need for any additional burdensome operations for assuring the expelling of the air from the filter.

Moreover, the filter device of the present invention has not any complicated structures in connection with the inlet and outlet of the casing, differing from the conventional filter devices, such as those of U.S. Pat. Nos. 4,923,620 and 5,092,996. Therefore, the filter device of the present invention is extremely simple in structure. Accordingly, the filter device of the present invention is advantageous in that not only is it very easy to produce, but also is free from the danger of breakage, as compared to the conventional filter devices.

In the filter device of the present invention, it is preferred that the inlet and the outlet be positioned as close to each other as possible. It is also preferred that the inlet and the outlet be positioned in a substantially symmetrical relationship with respect to a plane containing the central axis of the casing and extending in parallel to the main wall on the side of the outlet-side chamber, namely, a plane vertically passing through the filter medium along the thickness thereof.

In the leukocyte-removing filter device of the present invention, the structure of the inlet for blood and the structure of the outlet for leukocyte-removed blood are not particularly limited. Each of the inlet and the outlet may be independently a simple hole formed on the surface of a top portion of the casing or a nozzle stemming out of the surface of the casing on its top portion. A hole-type inlet or outlet is advantageous in that it can be easily formed because of a simple structure thereof. With respect to the hole-type inlet or outlet, when a blood circuit tubing (usually made of a pliable material) is connected to the casing, a connection is performed by squeezing an end portion of the circuit tube and inserting the squeezed end portion into the hole-type inlet or outlet of the casing. However, this type of connection is relatively weak, so that the inserted end portion is sometimes disconnected from the casing when strongly pulled. By contrast, the nozzle-type inlet or outlet is advantageous in that a blood circuit tube can be easily connected to the nozzle by widening the opening of the end portion of the circuit tube and tightly fitting the widened opening around the outer periphery of the nozzle, thereby ensuring a strong connection which is less likely to break.

In the leukocyte-removing filter device of the present invention, it is preferred that the length of each of the inlet and the outlet (that is, the distance between the open end of each of the inlet and the outlet on the outer side of the casing and the lower end of the opening thereof on the inner side of the casing, which is indicated by character $a$ in FIG. 1) be as small as possible to thereby render compact the structure of the filter and to minimize the danger of any damage to the inlet and outlet. More specifically, the length of each of the inlet and the outlet is preferably 50 mm or less, more preferably 30 mm or less, and still more preferably 15 mm or less. With respect to the nozzle-type inlet or outlet, for attaining a strong connection with a blood circuit tube, it is preferred that the length of each of the inlet and the outlet to be not less than 10 mm.

As mentioned above, in the filter device of the present invention, it is preferred that the inlet opens in a direction along a first line and the outlet opens in a direction along a second line, and the first and second lines each form an angle with the central axis extending vertically from the top portion to the bottom portion of the casing, wherein each angle being independently not more than 90° inclusive of 0° relative to the central axis, preferably 60° or less, more preferably 30° or less. Most preferably, each of the inlet and the outlet opens in a direction substantially parallel to the central axis of the casing, that is, at an angle of 0° relative to the central axis.

When the filter device of the present invention is accommodated in a centrifuge cup together with a plurality of blood bags in a state in which the filter device is held between the blood bags, the casing preferably has a shape such that it can fit well between the blood bags so that it can be easily and stably disposed in a centrifuge cup. Such shapes include a square and a rectangular shape in cross-section.

The outer dimensions of the casing is preferably not more than those of the customary blood bags. That is, it is preferred that the casing have the following outer dimensional characteristics: a width of not more than 15 cm, a height of not more than 25 cm and a thickness of not more than 2 cm. Considering the inner dimensions of a centrifuge cup, the casing is more preferably 10 cm or less in width and 15 cm or less in height. Further, considering the fact that the filter device is accommodated into a centrifuge cup together with a plurality of blood bags including a blood collection bag containing whole blood (inner volume: about 200 ml to about 600 ml), the inner volume of the filter casing is preferably not more than 150 ml. On the other hand, for attaining a satisfactorily high capability to remove leukocytes, the inner volume of the casing is preferably 1 ml or more, more preferably from 2 ml to 50 ml, still more preferably from 5 ml to 25 ml. Likewise, the thickness of the casing is more preferably from 0.1 cm to 1.5 cm, still more preferably from 0.2 cm to 1.0 cm and most preferably from 0.3 cm to 0.6 cm.

It is also preferred that the filter casing have a handle means therearound or in the top portion thereof for easy handling of the filter device, for example, in the removal of the filter device from the centrifuge cup after centrifugation.

When the filter device is placed above the blood bags in a centrifuge cup, the casing of the filter device is preferred to have a circular shape in cross-section or a regular polygonal shape (having 5 sides or more) in cross-section, and the diameter of the circle or polygon is preferably smaller than an inscribed circle of the centrifuge cup. Specifically, it is preferred that the casing have a circular shape (in cross-section) having a diameter of 10 cm or less, more preferably 8 cm or less, or a regular polygonal shape which can be inscribed in such a circular shape. Further, as described in U.S. Pat. No. 5,092,996, the casing may have a flange (support means) formed around the periphery of the casing in unified fashion so that the flange engages the upper circumference of the centrifuge cup when the filter is placed above the blood bags. Also with respect to the filter device which is to be placed above the blood bags in a centrifuge cup, the same preferred ranges of the inner volume and the outer dimensional characteristics as mentioned above can apply.

From the viewpoint of minimizing the danger of damaging the blood bags when the filter device is packed together with a plurality of blood bags in a centrifuge cup, it is preferred that the overall outer surface of the casing be substantially free of convexo-concave portions and sharp projections, rendering smooth the overall outer surface.

Furthermore, it is preferred that each of the inlet and the outlet be positioned within a space formed between two planes respectively extending along the outer surfaces of the two opposite flat main walls of the casing. When the nozzle-shaped inlet or outlet has a portion extending outwardly of the above-mentioned space, the portion is preferred to have a curvature so that the portion on a whole extends in parallel to the plane extending along the outer surface of the respective flat main wall.

With respect to the inner structure of the leukocyte-removing filter device of the present invention, the inlet-side chamber and outlet-side chamber (respectively designated with numerals 7 and 7' in FIG. 1) of the internal space of the casing serve to realize that the introduced blood spreads evenly over the surface of the filter medium on the side of the inlet-side chamber and the blood coming-out from the surface of the filter medium on the side of the out-side chamber flows into the outlet smoothly. For reducing the entire inner volume of the filter device, the thickness of each of the above-mentioned two chambers is preferably as small as possible, as long as the respective functions of the chambers are satisfactorily performed. Specifically, the inner thickness of each of the inlet-side chamber and the outlet-side chamber is preferably not more than 5 mm, more preferably not more than 2.5 mm. Particularly, the inner thickness of the outlet-side chamber is still more preferably not more than 1 mm.

The attainment of expulsion of the air in the filter device of the present invention varies depending on the structure of the outlet-side chamber of the filter device. For facilitating the air expulsion, it is desirable that the outlet-side chamber does not discontinuously vary in horizontal cross-sectional area more than 10% over the entire inner space of the outlet-side chamber from its inner bottom portion to its inner uppermost portion and wherein the inner uppermost portion of the outlet-side chamber decreases in horizontal cross-sectional area toward the outlet.

The inlet-side chamber is desired to have substantially the same configuration as that of the outlet-side chamber, from the viewpoint of ease in production of the filter device and the effective utilization of a filter medium for removing leukocytes.

In this connection, however, it is to be noted that the distance between the filter medium and the inner wall of the inlet-side chamber at its upper portion is preferably slightly larger than that at a lower portion of the inlet-side chamber. When the inlet-side chamber has this configuration, any blood-clogging of the upper portion of the filter medium on the side of the inlet-side chamber (clogging due to agglutination of blood which is likely to occur when good mixing of whole blood and an anticoagulant is not achieved in the whole blood collection bag) can be effectively avoided, thereby enabling blood to flow smoothly within the entire filter medium. A filter device having this feature is used in Example 1 described below.

Six representative forms of the leukocyte-removing filter device of the present invention are shown in FIG. 2(a) to 2(f), respectively. FIG. 3(a) to 3(f) are graphs showing the relationships between the horizontal cross-sectional areas of the outlet-side chambers of the filter devices respectively shown in FIGS. 2(a) to 2(f) and the vertical positions of the horizontal cross-sections measured with respect to the abovementioned areas. In each of FIG. 3(a) to FIG. 3(f), the outlet-side chamber does not discontinuously vary in horizontal cross-sectional area more than 10% over all of the inner space of the outlet-side chamber from its inner bottom portion to its inner uppermost portion.

Figure 2D:
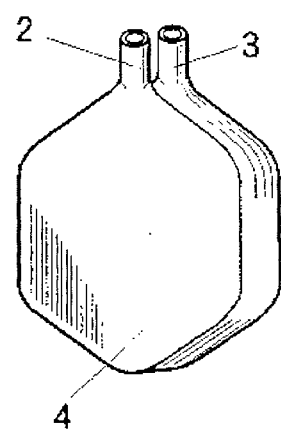
Figure 2E:
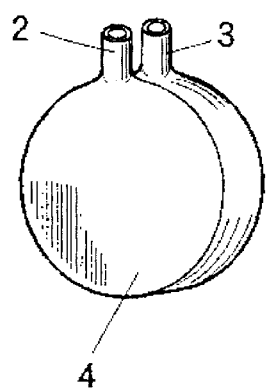
Figure 2F:
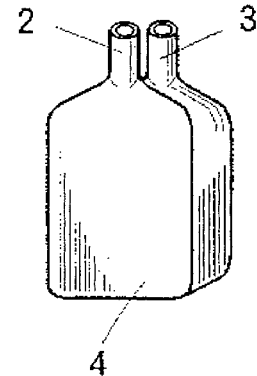
Figure 3A:
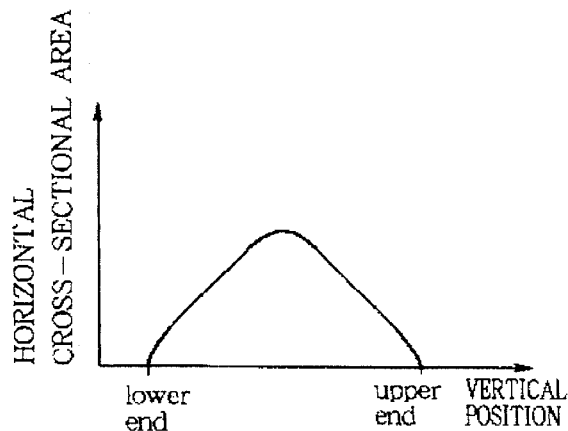
FIGS. 3(a) to 3(f) are graphs showing the relationships between the horizontal cross-sectional areas of the outlet-side chambers of the filter devices respectively shown in FIGS. 2(a) to 2(f) and the vertical positions of the horizontal cross-sections measured with respect to the above-mentioned areas.
Figure 3B:
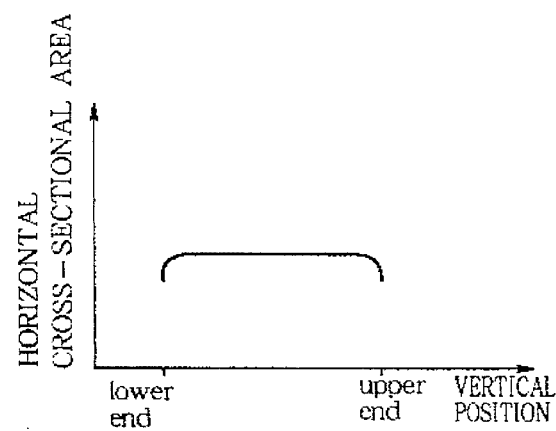
Figure 3C:
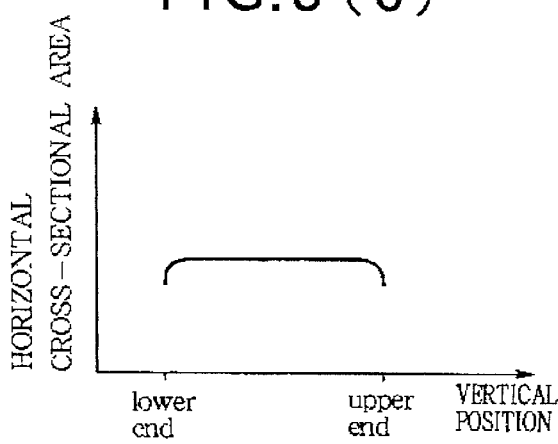
Figure 3D:
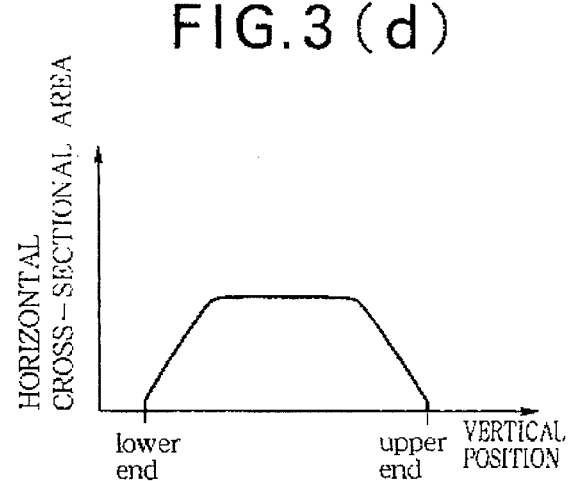
Figure 3E:
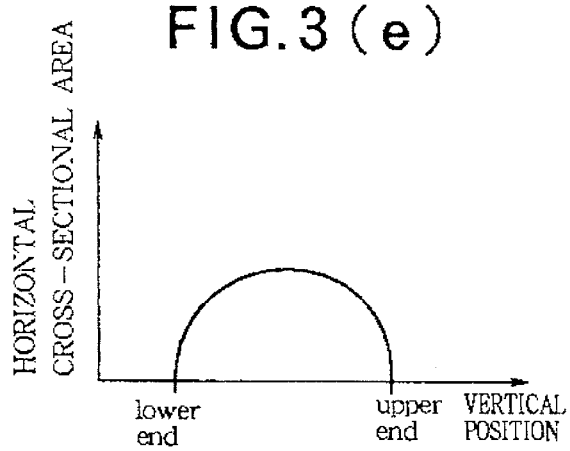
Figure 3F:
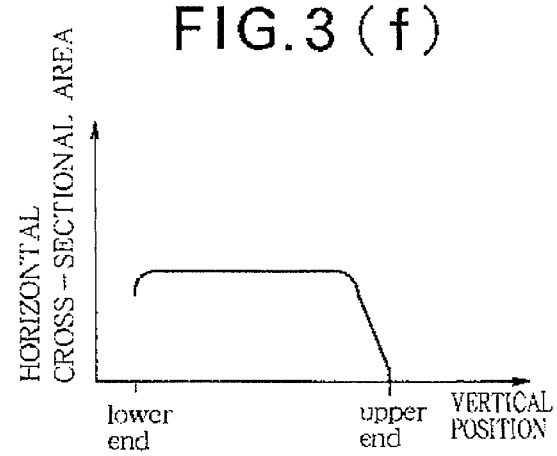

In FIG. 3(a) and FIGS. 3(d) to 3(f) respectively showing the horizontal cross-sectional area distributions of the outlet-side chambers of the filter devices of FIGS. 2(d) to 2(f) along the vertical direction thereof, the inner uppermost portion of the outlet-side chamber decreases in horizontal cross-sectional area toward the outlet so that the expulsion of the air in the filter device can be most easily achieved. Accordingly, the embodiments of FIG. 2(a) and FIGS. 2(d) to 2(f) are more preferred than the embodiments of FIGS. 2(b) and 2(c). The embodiment of FIG. 2(f) having a shape which resembles a baseball home plate turned upside down is especially preferred, because it can be very fittedly and stably accommodated in a centrifuge cup.

In producing the casing, any of the customary materials can be used as long as the materials do not have an adverse effect on blood. Generally, relatively rigid materials, such as polycarbonate resins and acrylic resins, which are effective in keeping uniform the thickness of a filter medium, are advantageously employed. When a filter medium employed is one which has been processed so as to be able to retain a uniform thickness, the material for the casing may suitably be selected from relatively pliable materials, such as pliable polyvinyl chloride. The use of a pliable material is advantageous from the viewpoint of minimizing the danger of damaging the filter device and the blood bags during centrifugation. In the present invention, the outer surface of the flat casing may contain a curvature which can fit the inner surface of the centrifuge cup. The use of a pliable material for the casing is advantageous in that the casing allows more fitted contact with the inner surface of a centrifuge cup by virtue of the pliable nature of the material of the casing. As a criterion for judging the rigidness or a pliableness of a material, a hardness value can be used, which is obtained by a hardness testing in which a spring-type hardness testing machine (described in JIS K6301, the item of Hardness Testing) is employed. A material exhibiting a hardness value of 100 degrees or more can be classified as a rigid material and a material exhibiting a hardness value of less than 100 degrees can be classified as a pliable material.

With respect to the leukocyte-removing filter device of the present invention, the filter material sheet as a filter medium can be selected from a wide variety of known porous elements, such as fibrous porous material (e.g., a woven or nonwoven fabric) and a porous material having a three-dimensional network of continuous pores. Further, there is no particular limitation with respect to the structure of the filter material sheet. For example, the filter material sheet may be comprised of a single porous element. Also, the filter material sheet may be comprised of a plurality of porous elements having different average pore diameters which are laid upon one another so that the average pore diameter of the filter medium on a whole decreases from the side of the inlet-side chamber toward the side of the outlet-side chamber. Further, the filter material sheet may be comprised of a plurality of identical porous elements having a same average pore diameter.

The filter medium accommodated in the filter device may be in a dry state. However, it is more preferred that the filter medium be in a state moistened with a physiological liquid to a degree such that the filter medium is saturated therewith.

The maximum volume of blood which can be contained in the filter device is preferably 20% or less, more preferably 10% or less, based on the total volume of blood material to be treated by the filter device (generally, from 50 ml to 600 ml). Further, the maximum volume of blood which occupies the inlet-side and outlet-side chambers of the internal space (exclusive of the filter medium) of the filter device is preferably 30% or less, more preferably 10% or less, based on the above-mentioned maximum volume of blood which can be contained in the filter device.

The manner of use of the leukocyte-removing filter device of the present invention is not particularly limited. The filter device of the present invention can be used in the same manner as employed for the conventional filters. For example, the leukocyte-removing filter device of the present invention can be used not only for removing leukocytes from blood for transfusion, but also for therapy by extracorporeal circulation leukocyte removal (Nishimura, T., Polymer Materials for Blood Purification, in Biomedical Applications of Polymeric Materials, Edited by Tsuruta, T., et al., CRC Press, Boca Raton, 1993, p. 191–218).

Further, the filter device of the present invention may be incorporated into a known leukocyte-removing system comprising a filter and at least one blood bag, in substitution for the conventional filter. Examples of such known filter systems include the filter system disclosed in U.S. Pat. No. 4,596,657. By the use of the filter device of the present invention, it becomes very easy to fittedly and stably accommodate a filter system in a centrifuge cup, so that not only is the filter device unlikely to be out of the centrifuge cup, but also the filter device and the blood bags are not damaged.

The filter device of the present invention can be incorporated into a wide variety of known leukocyte-removing systems which can be used for removing leukocytes from blood before the storing of the blood.

Accordingly, in another aspect of the present invention, there is provided a leukocyte-removing system comprising:

a leukocyte-removing filter device comprising:
 (a) a flat casing comprising opposite flat main walls fluid-tightly connected by a side wall structure to define an internal space of the casing, the casing having a top and a bottom portion which are spaced apart vertically of the casing, the top portion having an inlet for blood and an outlet for leukocyte-removed blood, and (b) a filter medium comprising at least one filter material sheet extending in the internal space of the casing along the flat main walls to partition the internal space into an inlet-side chamber communicated with the inlet and an outlet-side chamber communicated with the outlet, inlet connecting means fluid-tightly connected to the inlet for aseptically connecting a part preceding the leukocyte-removing filter device to the inlet, at least one satellite bag, and outlet connecting means for fluid-tightly directly connecting the outlet of the leukocyte-removing filter device to the at least one satellite bag, the outlet connecting means comprising a tube, wherein the leukocyte-removing system is entirely in an aseptic state.

The leukocyte-removing system of the present invention can advantageously be used to aseptically remove leukocytes from blood before the storing of the blood. By using the system of the present invention, the leukocyte removal operation can be very effectively and efficiently conducted by virtue of the presence of the leukocyte-removing filter device of the present invention. When the leukocyte-removing filter device is placed in a centrifuge cup together with a plurality of blood bags for centrifugal separation of blood, the entire system can be fittedly and stably accommodated in the centrifuge cup with ease. In this instance, the filter device is unlikely to be out of the centrifuge. In addition, the filter device and blood bags are unlikely to suffer from damage. In the leukocyte removal operation using the system of the present invention, the expulsion of the air in the filter device at the time of start of the filtering operation can be readily performed simply by allowing blood to flow into the filter device without any additional burdensome operations.

FIGS. 5(a)–5(d) are diagrams showing preferred embodiments of the system of the present invention which are particularly useful for a leukocyte-removing operation in which collected whole blood is first subjected to centrifugation to obtain a red cell concentrate and leukocytes are aseptically removed from the red cell concentrate. In FIGS. 5(a) to 5(d), the leukocyte-removing system is comprised of an anticoagulant-containing blood collection bag 8, satellite bags 9 and 9' or 9, 9' and 9" and leukocyte-removing filter device 1 or filter devices 1 and 1'. The satellite bag 9 is connected to blood collection bag 8 through filter device 1. The remaining satellite bag(s), i.e. satellite bag 9' or satellite bags 9'and 9", are connected to blood collection bag 8 not through any filter device, but directly in the case of FIGS. 5(a) to 5(c) or through filter device 1' in the case of FIG. 5(d).

Figure 5A:
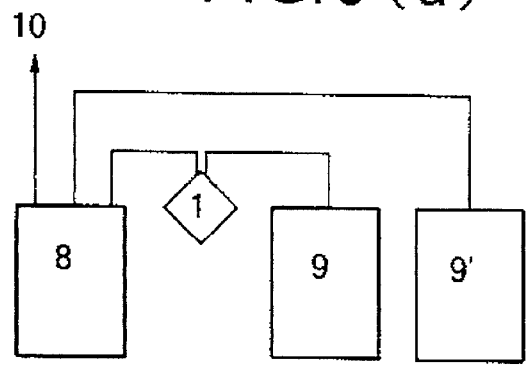
FIGS. 5(a) to 5(d) are diagrams showing embodiments of the leukocyte-removing systems of the present invention, in which at least one satellite bag is connected to a blood collection bag through the filter device and at least one satellite bag is directly connected to the blood collection bag.
Figure 5B:
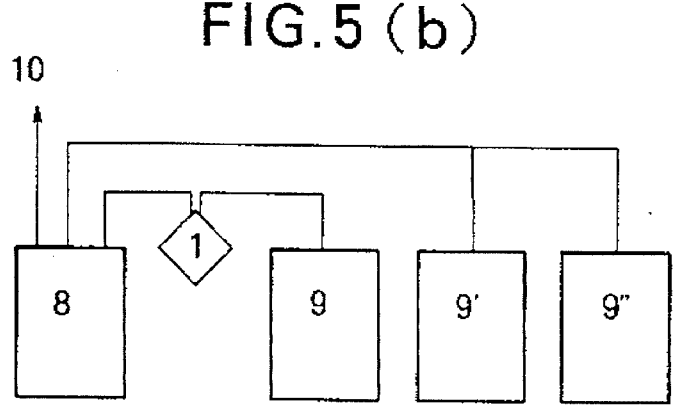
Figure 5C:
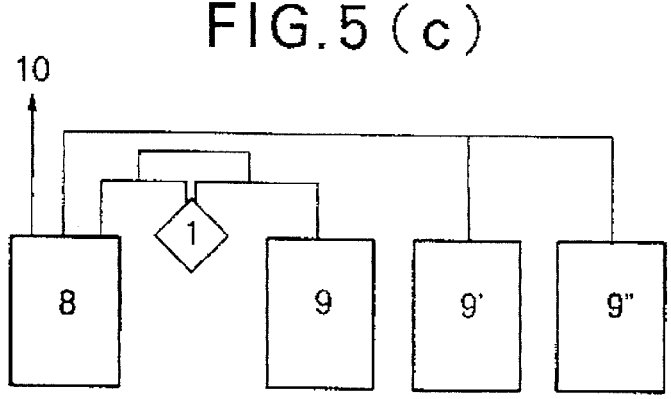
Figure 5D:
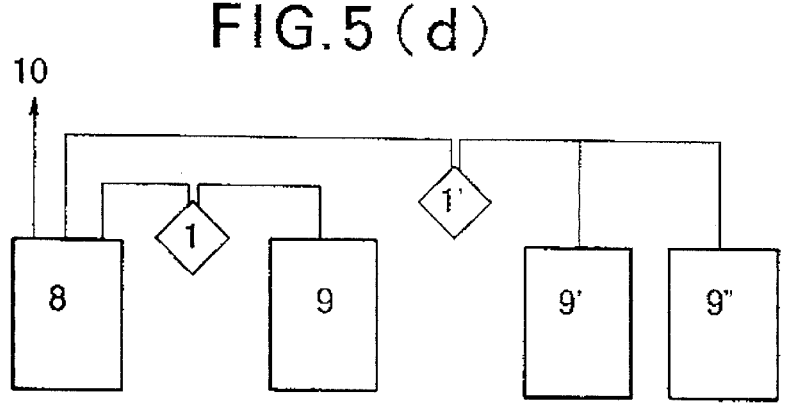

In operation, fresh whole blood is introduced from a donor into an anticoagulant-containing blood collection bag 8 through cannula 10, and is mixed well with the anticoagulant in bag 8. Upon collection of the fresh whole blood, cannula 10 is disconnected after sealing a tube (connecting cannula 10 to blood collection bag 8) by means of a heat-sealer or the like. Then, the entire system is accommodated in a centrifuge cup, as shown in FIG. 4, and subjected to centrifugation. After centrifugation, the system is gently taken out of the centrifuge cup. The upper layer in bag 8 composed of plasma component is transferred into satellite bag 9'. (When the centrifugal force is relatively strong, the plasma obtained is platelet-poor plasma, whereas when the centrifugal force is relatively weak, the plasma obtained is platelet-rich plasma.) Then, a lower layer in bag 8 composed of a red cell concentrate in bag 8 is passed through filter device 1 to remove leukocytes from the red cell concentrate. The resultant leukocyte-removed red cell concentrate is received by bag 9. In the systems of FIGS. 5(b) to 5(d), when the plasma in bag 9' is platelet-rich plasma, the plasma in bag 9' is further subjected to centrifugation, thereby obtaining a platelet concentrate and platelet-poor plasma, and the latter is transferred to bag 9".

In the systems shown in FIGS. 5(a) to 5(d), a preservative liquid for red cells may be contained in any of satellite bags 9, 9' and 9". It is also preferred that the red cell preservative liquid be added to the red cell concentrate contained in bag 8 before blood filtration.

In the system shown in FIG. 5(c), in order to return the air accumulated in satellite bag 9 into bag 8, a bypass tube which bypasses filter device 1 is connected as depicted in FIG. 5(c). That is, the bypass is connected, at one end thereof, to a tube [hereinafter referred to "tube (1)"] between bag 8 and filter device 1 and, at the other end thereof, to a tube [hereinafter referred to as "tube (2)"] between filter device 1 and satellite bag 9. The bypass tube has valve means (or cramp means). When the blood is transferred from bag 8 to bag 9 through the filter device 1, the valve means of the bypass tube is closed, and when the air accumulated in bag 9 is returned to bag 8, the valve means of the bypass tube is opened. The air returned from bag 9 does not pass through filter device 1 since the filter medium is in a wet state with blood. For preventing the anticoagulant in bag 8 from accidentally flowing into filter device 1 before the use of filter device 1, at least tube (1) of tubes (1) and (2) may have valve means at its portion between filter device 1 and a connecting point connecting the bypass tube to tube (1).

In the system shown in FIG. 5(d), filter device 1' is adapted to remove leukocytes, but allows platelets to pass therethrough. Therefore, in the system shown in FIG. 5(d), filter device 1' is useful to remove leukocytes from platelet-rich plasma obtained in bag 8.

As mentioned above and well known in the art, in a centrifugal operation, the manner of separation of blood components can be varied by changing the strength of the centrifugal force. This is possible due to the differences in specific gravity among blood components. For reference, the specific gravity of each of the blood components is given below:

specific gravity (i) leukocyte
  granulocyte 1.087–1.092*
  monocyte 1.065–1.068*
  lymphocyte 1.055–1.070*

(ii) erythrocyte (red cell) 1.093–1.096*

(iii) platelet 1.040–1.058*

(iv) plasma 1.025–1.029**

* Nishimura, T., Polymer Materials for Blood Purification, in Biomedical Applications of Polymeric Materials, Edited by Tsuruta, T., et al., CRC Press, Boca Raton, 1993, p. 209

** Koshikawa, S., Kessho Kokan Ryoho (Plasma Exchange Therapy)—Plasmapheresis '88, Shinko Koeki Co., Ltd., Japan, 1988, p. 115

Figure 6A:
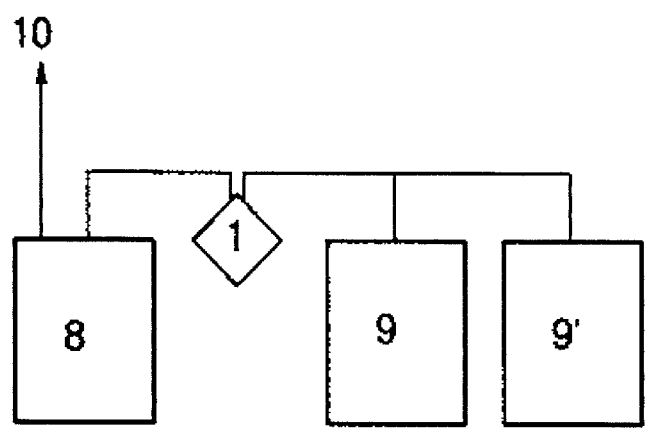
FIGS. 6(a) to 6(b) are diagrams showing further embodiments of the leukocyte-removing systems of the present invention, in which a plurality of satellite bags connected in series are connected to a blood collection bag (primary bag) through the filter device.
Figure 6B:
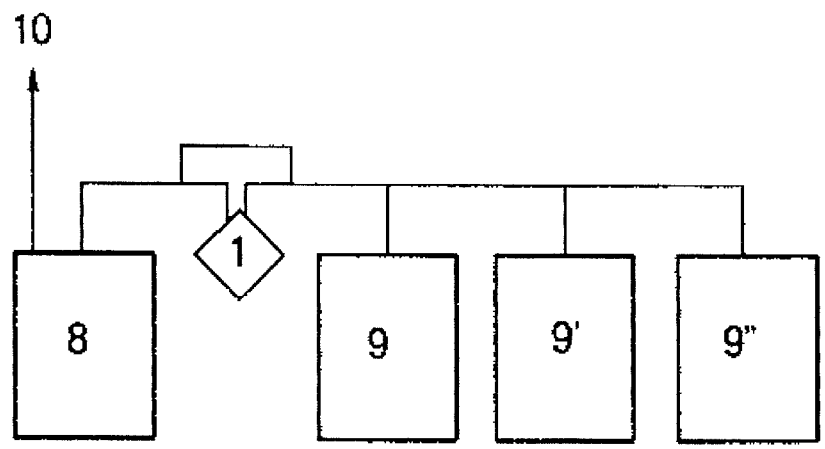

FIGS. 6(a) and 6(b) are diagrams showing further embodiments of the system of the present invention, which are particularly useful for a leukocyte-removing operation in which collected whole blood is first subjected to leukocyte removal treatment and the resultant leukocyte-removed blood is subjected to centrifugation so as to be separated into blood components. In FIGS. 6(a) and 6(b), the leukocyte-removing system is comprised of an anticoagulant-containing blood collection bag 8, a plurality of satellite bags 9 and 9' or 9, 9' and 9" connected in series and leukocyte-removing filter device 1. In these systems, all of the satellite bags are connected to blood collection bag 8 through leukocyte-removing filter device 1. The manner of use of these systems is similar to that disclosed in U.S. Pat. No. 4,985,153. Generally, these systems are used for obtaining a leukocyte-removed red cell concentrate is in satellite bag 9, and for obtaining leukocyte-removed plasma in satellite bag 9'. In the system shown in FIG. 6(b), by employing filter device 1 which is capable of removing leukocytes but also capable of allowing platelets to pass there-through, a leukocyte-removed platelet concentrate can be advantageously obtained in satellite bag 9".

Figure 7:
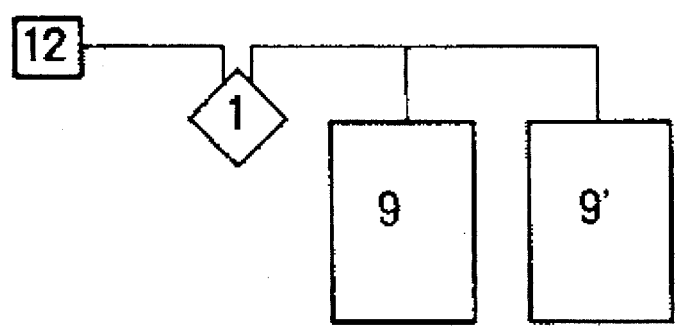
FIGS. 7(a) to 7(b) are diagrams showing still further embodiments of the leukocyte-removing systems of the present invention, in which the inlet of the filter device is connected to inlet connecting means for aseptically connecting a part preceding the filter device to the inlet of the filter device, and the outlet of the filter device has connected thereto a plurality of satellite bags connected in series.
Figure 7:
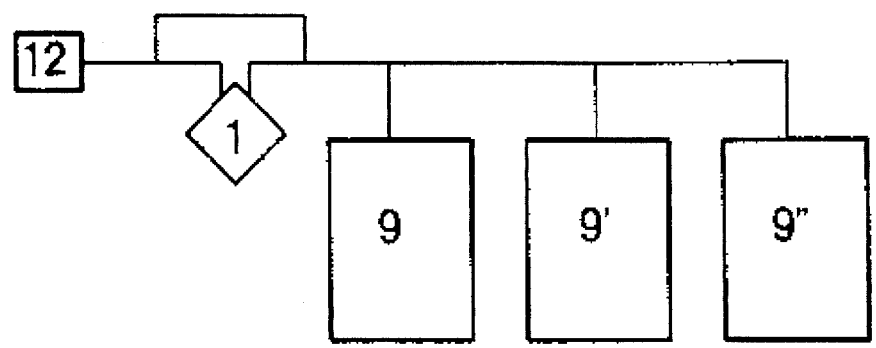

FIG. 7(a) and 7(b) are diagrams showing still further embodiments of the system of the present invention, in which the inlet of filter device 1 is connected to inlet connecting means 12 for aseptically connecting a part preceding filter device 1 to the inlet of filter device 1 and the outlet of filter device 1 has connected thereto a plurality of satellite bags 9 and 9' or 9, 9' and 9" connected in series.

The systems of FIGS. 7(a) and 7(b) are respectively the same as the systems of FIGS. 6(a) and 6(b) except that blood bag 8 and cannula 10 are not incorporated but inlet connecting means 12 is incorporated.

Illustrative examples of inlet connecting means for aseptically connecting a part preceding the filter device to the inlet of the filter device include those disclosed in U.S. Pat. No. 4,997,577 and WO 92/20427.

With respect to the systems shown in FIGS. 7(a) and 7(b), before a blood collection bag (as a part preceding the filter device) is connected to the system at inlet connecting means 12, whole blood is collected in the blood collection bag and a part of the blood can be subjected to blood testing. Therefore, in the case of the systems of FIGS. 7(a) and 7(b), whole blood to be treated by the systems can be limited to whole blood which has been qualified by the blood testing, thereby successfully solving the following problem accompanying the conventional leukocyte-removing systems. In the case of the conventional systems, since the blood collection bag is connected to the other components of the system in unified fashion, when it is desired to limit whole blood to be treated to whole blood which has been qualified by a blood testing, the blood testing has to be completed before the collection of whole blood. However, a blood testing usually takes as long as several hours to several days, so that a blood testing before collection of whole blood is impractical. Therefore, in the case of the conventional systems, a blood testing is frequently conducted after completion of the leukocyte-removing operation. In this case, when the leukocyte-removed blood cannot pass the blood testing, the entire system which has been contaminated during the filtration operation must be discarded.

Other examples of parts preceding the filter device include a filter for removing microorganisms and the like. The above-mentioned inlet connecting means need not necessarily be connected to any preceding part and the open end portion of the inlet connecting means can be sealed by means of a heat sealer or the like.

As describe above, in the leukocyte-removing filter device of the present invention, both of the inlet for blood and the outlet for leukocyte-removed blood are located in the top portion of the casing. By virtue of this novel feature, the filter device of the present invention can be fittedly and stably accommodated in a centrifuge cup together with a plurality of blood bags and circuit tubing connecting the filter device and blood bags, so that a centrifugation can be efficiently conducted without the danger of damaging the filter device and the blood bags. Moreover, the expelling of the air from the filter by filling the filter with blood can be very readily attained simply by allowing blood to flow into the filter without any additional burdensome operations. In addition, this filter is simple in structure and, therefore, is easy to produce.

The leukocyte-removing system of the present invention containing this novel filter device is extremely useful for aseptically removing leukocytes from blood before the storing of the blood.

PREFERRED EMBODIMENT OF THE INVENTION

The present invention will now be described in detail with reference to the following Example and Comparative Example, which should not be construed as limiting the scope of the present invention. Example 1

A non-woven fabric (Microweb® A066A, manufactured and sold by Asahi Kasei Kogyo Kabushiki Kaisha, Japan) of polyethylene terephthalate fibers having an average fiber diameter of 1.7 μm was cut into square sheets each having a size of 65 mm×65 mm. The thus obtained square sheets were piled upon one another to form a laminate sheet having a thickness of about 5 mm. As shown in FIG. 1 and FIG. 2(a), the laminate sheet (i.e., filter medium 5, 5') was packed in casing 4 made of polycarbonate, to thereby prepare leukocyte-removing filter device 1, in which both inlet 2 for blood and outlet 3 for leukocyte-removed blood was located at a top portion of casing 4.

Casing 4 was substantially the same as the casing of Sepacell® R-200 (II) (which is a tradename of a leukocyte-removing filter for blood transfusion manufactured and sold by Asahi Medical Co., Ltd., Japan) except that the casing material was polycarbonate in place of the styrene-butadiene block polymer used in Sepacell® R-200 (II), and that inlet 2 and outlet 3 were not located in the upper and lower end portions of the casing but located in the top portion of casing 4 as shown in FIG. 1 and FIG. 2(a). In the production of filter device 1, an inlet-side half section of the casing and an outlet-side half section of the casing were separately produced and then both half sections were arranged to face each other so as to enclose filter medium (5, 5') therein, followed by fluid-tight connection of both sections to each other by ultrasonic welding.

Casing 4 had the following outer dimensional characteristics: a square of 7.1 cm×7.1 cm and a thickness of 1.1 cm. Each of nozzle-shaped inlet 2 and nozzle-shaped outlet 3 had the following dimensional characteristics: an outer diameter of 6.5 mm, an inner diameter of 3.5 mm, a length (indicated by character $\underline{a}$ in FIG. 1) of 22 mm (a length of a portion protruding outwardly of the main body of casing 4 was 12 mm).

In casing 4, the depth of the inner peripheral groove (indicated by character in FIG. 1) is 3.5 mm and the effective filtering area of filter medium (5, 5') is 5.8 cm×5.8 cm. The height of projection 6 in inlet-side chamber 7 increased from 0.5 mm to 1.5 mm from the bottom portion toward inlet 2, and the height of projection 6' in outlet-side chamber 7' was evenly 0.6 mm.

Filter medium (5, 5') in a packed state had a thickness of 4.7 mm and a packing density of 0.20 g/cm$^3$.

The maximum volume of blood which could be contained in filter device 1 was 20 ml.

Using above-obtained leukocyte-removing filter device 1, and blood collection bag 8 containing a CPD (citrate phosphate dextrose) solution and satellite bags 9, 9' and 9" (a set of blood bags: Blood-Pac® Container Systems, manufactured and sold by Baxter Healthcare Corporation, U.S.A.), a leukocyte-removing system as shown in FIG. 5(b) was prepared. Into satellite bag 9, 100 ml of a red cell preservative liquid (ADSOL®, manufactured and sold Baxter Healthcare Corporation, U.S.A.) had previously been added.

The CPD solution in blood collection bag 8 was discharged. A mixture (500 ml) of 437 ml of bovine whole blood and 63 ml of CPD solution was charged into blood collection bag 8. Then, as shown in FIG. 4, filter device 1 was accommodated in centrifuge cup 11 (having an inner diameter of 10 cm and a depth of 15 cm) together with blood bags 8, 9, 9' and 9" so that filter device 1 was disposed between blood collection bag 8 and satellite bag 9, and both inlet 2 and outlet 3 of filter device 1 were directed upward and positioned at the upper portion of centrifuge cup 11.

Centrifuge cup 11 containing filter device 1 and bags 8, 9, 9' and 9" was subjected to centrifugation at a centrifugal force of 4400 G for 10 minutes, using a centrifuge (CR783, manufactured and sold by Hitachi Koki Co., Ltd., Japan), thereby separating the blood into an upper layer and a lower layer. Thereafter, the upper layer composed of plasma in blood collection bag 8 was transferred into satellite bag 9' (which was not connected to filter device 1). Then, blood collection bag 8 was lifted to and hung at a height of 1.5 m, and the lower layer composed of a red cell concentrate in blood collection bag 8 was allowed to flow into filter device 1 by gravity. The leukocyte-removed red cell concentrate from filter device 1 was collected in satellite bag 9.

The same procedure as described above (i.e., the production of a leukocyte-removing system and an experiment using the same) was repeated 10 times. As a result, it was found that, in each time, filter device 1 could be readily, fittedly and stably accommodated into centrifuge cup 11 together with bags 8, 9, 9' and 9", and the centrifugation could be conducted without causing any damage to filter device 1 and bags 8, 9, 9' and 9". The operation of expelling the air from filter device 1 by filling filter device 1 with blood could also be very readily performed simply by allowing blood to flow into filter device 1 without any additional burdensome operations. In addition, the flowing of blood in filter device 1 was very smooth.

Comparative Example

Substantially the same procedure as in Example was repeated except that use was made of a filter device having an inlet and an outlet in upper and lower ends of the casing of the filter device, respectively. The filter device was placed in a centrifuge cup in the same manner as in FIG. 4, except that the outlet was directed downward.

As a result, it was found that the operation for accommodating the filter device together with blood bags in the centrifuge cup was cumbersome. Further, in six experiments of the ten times-repeated experiments, a damage to the filter device and/or the blood bags was observed after centrifugation. Even in the remaining experiments in which the filter device and bags were not damaged during centrifugation, the expulsion of the air in the filter device was unable to be achieved simply by utilizing the force of gravity. Further, the flow rate of blood in the filter device was slightly low as compared to that in the case of filter device 1 of Example 1, but exhibited a decrease in the course of the filtration. In some cases, the decrease in the flow rate was so large as not to be acceptable.

What is claimed is:

1. A leukocyte-removing filter device comprising:
   (a) a flat casing comprising opposite flat main walls fluid-tightly connected by a side wall structure to define an internal space of said casing, each main wall vertically extending and having a width and a height, said side wall structure having a width defined by a distance between said opposite flat main walls, wherein said casing has a top and a bottom portion which are spaced apart vertically of said casing, and wherein the width or height of each main wall, whichever is shorter, is at least two times the width of the side wall structure,
   said top portion having an inlet for blood and an outlet for leukocyte-removed blood, and
   said top portion vertically extending from a top end of said casing over a length one-third or less the entire vertical length of the casing as measured from the top end of the casing; and
   (b) a filter medium comprising at least one filter material sheet extending within said internal space of the casing along said flat main walls to partition said internal space into an inlet-side chamber communicating with said inlet and an outlet-side chamber communicating with said outlet, said outlet-side chamber not discontinuously varying in horizontal cross-sectional area more than 10% over the entire inner space of the outlet-side chamber from its inner bottom portion to its inner uppermost portion.

2. The filter device according to claim 1, wherein the casing has a central axis vertically extending from said top portion to said bottom portion, and the inlet opens in a direction along a first line and the outlet opens in a direction along a second line, said first and second lines each forming an angle with the central axis and each angle being independently not more than 90° inclusive of 0° relative to the central axis.

3. The filter device according to claim 2, wherein each of said inlet and said outlet opens in a direction substantially parallel to the central axis of the casing.

4. The filter device according to claim 2, wherein said inlet and said outlet are positioned in a symmetrical relationship with respect to a plane containing the central axis of the casing and extending in parallel to the main wall on the side of said outlet-side chamber.

5. The filter device according to claim 1, wherein the overall outer surface of said casing is substantially free of convexo-concave portions and sharp projections, rendering smooth said overall outer surface, and wherein said casing has an inner volume of from 1 ml to 150 ml and has the following outer dimensional characteristics: a width of not more than 15 cm, a height of not more than 25 cm and a thickness of not more than 2 cm.

6. The filter device according to claim 1, wherein the inner uppermost portion of said outlet-side chamber decreases in horizontal cross-sectional area toward said outlet.

7. The system according to claim 1, wherein the bottom, inside portion of the sidewall structure is provided with a groove for accommodating the bottom portion of the filter material sheet.

8. The system according to claim 1, wherein the internal walls of the sidewall structure of said inlet-side chamber and said outlet-side chamber are provided with pressing means.

9. The system according to claim 8, wherein the pressing means are a plurality of projections extending from the sidewall structure toward the filter medium.

10. The system according to claim 8, wherein the pressing means is a loose, resiliently disposed mesh-like structure.

11. A leukocyte-removing system comprising:
a leukocyte-removing filter device comprising:
(a) a flat casing comprising opposite flat main walls fluid-tightly connected by a side wall structure to define an internal space of said casing, each main wall vertically extending and having a width and a height, said side wall structure having a width defined by a distance between said opposite flat main walls, wherein said casing has a top and a bottom portion which are spaced apart vertically of said casing, and wherein the width or height of each main wall, whichever is shorter, is at least two times the width of the side wall structure, said top portion having an inlet for blood and an outlet for leukocyte-removed blood, and said top portion vertically extending from a top end of said casing over a length one-third or less the entire vertical length of the casing as measured from the top end of the casing; and (b) a filter medium comprising at least one filter material sheet extending within said internal space of the casing along said flat main walls to partition said internal space into an inlet-side chamber communicating with said inlet and an outlet-side chamber communicating with said outlet, said outlet-side chamber not discontinuously varying in horizontal cross-sectional area more than 10% over the entire inner space of the outlet-side chamber from its inner bottom portion to its inner uppermost portion, inlet connecting means fluid-tightly connected to the inlet for aseptically connecting a part preceding the leukocyte-removing filter device to said inlet, at least one satellite bag, and outlet connecting means for fluid-tightly directly connecting said outlet of the leukocyte-removing filter device to said at least one satellite bag, said outlet connecting means comprising a tube, wherein said leukocyte-removing system is entirely in an aseptic state.

12. The system according to claim 11, further having an anticoagulant-containing blood collection bag fluid-tightly connected to said inlet connecting means, and wherein said at least one satellite bag includes a plurality of satellite bags connected in series.

13. The system according to claim 1, further having an anticoagulant-containing blood collection bag fluid-tightly connected to said inlet connecting means and having at least one satellite bag fluid-tightly, aseptically connected to said blood collection bag.

14. A method for removing leukocytes from blood, which comprises the steps of:
(1) providing a leukocyte-removing filter device comprising:
(a) a flat casing comprising opposite flat main walls fluid-tightly connected by a side wall structure to define an internal space of said casing, each main wall vertically extending and having a width and a height, said side wall structure having a width defined by a distance between said opposite flat main walls, wherein said casing has a top and a bottom portion which are shaped apart vertically of said casing, and wherein the width or height of each main wall, whichever is shorter, is at least two times the width of the side wall structure, said top portion having an inlet for blood and an outlet for leukocyte-removed blood, and said top portion vertically extending from a top end of said casing over a length one-third or less the entire vertical length of the casing as measured from the top end of the casing, and (b) a filter medium comprising at least one filter material sheet extending within said internal space of the casing along said flat main walls to partition said internal space into an inlet-side chamber communicating with said inlet and an outlet-side chamber communicating with said outlet, said outlet-side chamber not discontinuously varying in horizontal cross-sectional area more than 10% over the entire inner space of the outlet-side chamber from its inner bottom portion to its inner uppermost portion;

(2) allowing blood to flow into the inlet of said filter device and pass through said filter medium contained in said filter device to thereby remove leukocytes from the blood, and discharging leukocyte-removed blood from the outlet of said filter device.

15. A method for removing leukocytes from blood, which comprises the steps of:
(1) providing at least one leukocyte-removing system comprising:
(A) a leukocyte-removing filter device comprising:
(a) a flat casing comprising opposite flat main walls fluid-tightly connected to a side wall structure to define an internal space of said casing, each main wall vertically extending and having a width and a height, said side wall structure having a width defined by a distance between said opposite flat main walls, wherein said casing has a top and a bottom portion which are spaced apart vertically of said casing, and wherein the width or height of each main wall, whichever is shorter, is at least two times the width of the side wall structure, said top portion having an inlet for blood and an outlet for leukocyte-removed blood, and said top portion vertically extending from a top end of said casing over a length one-third or less the entire vertical length of the casing as measured from the top end of the casing, and (b) a filter medium comprising at least one filter material sheet extending within said internal space of the casing along said flat main walls to partition said internal space into an inlet-side chamber communicating with said inlet and an outlet-side chamber communicating with said outlet, said outlet-side chamber not discontinuously varying in horizontal cross-sectional area more than 10% over the entire inner space of the outlet-side chamber from its inner bottom portion to its inner uppermost portion, (B) inlet connecting means fluid-tightly connected to the inlet for aseptically connecting a part preceding the leukocyte-removing filter device to said inlet, (C) at least one satellite bag, and (D) outlet connecting means for fluid-tightly directly connecting said outlet of the leukocyte-removing filter device to said at least one satellite bag, said outlet connecting means comprising a tube;

(2) allowing blood to flow into the inlet of said filter device through said inlet connecting means,and pass through said filter medium contained in said filter device to thereby remove leukocytes from the blood, and discharging leukocyte-removed blood from the outlet of said filter device; and (3) transferring leukocyte-removed blood to said at least one satellite bag through said outlet connecting means.

16. The method according to claim 15, wherein said at least one leukocyte-removing system further comprises a blood collection bag which is directly or indirectly connected to said inlet connecting means fluid-tightly connected to the inlet of said filter device, which method further comprises, prior to said step (2):

providing a centrifugal apparatus comprising at least one centrifuge cup;

placing the blood to be flowed through said filter device in said blood collection bag of said at least one leukocyte-removing system;

accommodating said at least one leukocyte-removing system in said at least one centrifuge cup of said centrifugal apparatus, respectively, wherein said filter device is held between said blood collection bag and said at least one satellite bag in a vertically directed configuration, or placed on said blood collection bag and said at least one satellite bag; and actuating said centrifugal apparatus to thereby centrifuge said blood contained in said blood collection bag.

* * * * *